(12) United States Patent
Van Den Berg

(10) Patent No.: US 6,378,521 B1
(45) Date of Patent: Apr. 30, 2002

(54) ARTIFICIAL AIRWAY DEVICE

(75) Inventor: Paulus Cornelis Maria Van Den Berg, Amsterdam (NL)

(73) Assignee: Ideamed N.V., Curacao (AN)

( * ) Notice: Subject to any disclaimer, the term of this patent is extended or adjusted under 35 U.S.C. 154(b) by 0 days.

(21) Appl. No.: 09/308,811

(22) PCT Filed: Nov. 24, 1997

(86) PCT No.: PCT/NL97/00641

§ 371 Date: Jul. 22, 1999

§ 102(e) Date: Jul. 22, 1999

(87) PCT Pub. No.: WO98/23317

PCT Pub. Date: Jun. 4, 1998

(30) Foreign Application Priority Data

Nov. 28, 1996 (NL) ................................................ 10046

(51) Int. Cl.[7] ............................ A61M 16/00; A62B 9/06
(52) U.S. Cl. ............................ 128/207.14; 128/200.26; 128/207.15
(58) Field of Search ..................... 128/200.26, 207.14, 128/207.15

(56) References Cited

U.S. PATENT DOCUMENTS

| | | | | |
|---|---|---|---|---|
| 2,541,691 A | | 6/1951 | Eicher | |
| 3,169,529 A | * | 2/1965 | Koenig | 128/207.15 |
| 3,616,799 A | * | 11/1971 | Sparks | 128/207.15 |
| 3,799,173 A | * | 3/1974 | Kamen | 128/207.15 |
| 4,150,676 A | * | 4/1979 | Jackson | 128/207.15 |
| 4,449,522 A | * | 5/1984 | Baum | 128/200.26 |
| 4,449,523 A | * | 5/1984 | Szachowicz et al. | 128/200.26 |
| 4,589,410 A | * | 5/1986 | Miller | 128/207.15 |
| 4,637,389 A | * | 1/1987 | Heyden | 128/207.15 |
| 4,672,960 A | * | 6/1987 | Frankel | 128/200.26 |
| 4,700,700 A | * | 10/1987 | Eliachar | 128/207.15 |
| 4,840,172 A | | 6/1989 | Augustine et al. | |
| 4,886,059 A | * | 12/1989 | Weber | 128/207.15 |
| 5,020,534 A | * | 6/1991 | Pell et al. | 128/207.15 |
| 5,076,268 A | * | 12/1991 | Weber | 128/207.15 |
| 5,241,956 A | * | 9/1993 | Brain | 128/207.15 |
| 5,303,697 A | * | 4/1994 | Brain | 128/200.26 |
| 5,355,879 A | * | 10/1994 | Brain | 128/207.15 |
| 5,443,063 A | * | 8/1995 | Greenberg | 128/207.15 |
| 5,477,851 A | * | 12/1995 | Callaghan et al. | 128/207.15 |
| 5,477,852 A | * | 12/1995 | Landis et al. | 128/207.18 |
| 5,513,627 A | * | 5/1996 | Flam | 128/200.26 |
| 5,514,153 A | | 5/1996 | Bonutti | |
| 5,584,290 A | * | 12/1996 | Brain | 128/207.15 |
| 5,623,921 A | * | 4/1997 | Kinsinger et al. | 128/200.26 |
| 5,632,271 A | * | 5/1997 | Brain | 128/207.15 |
| RE35,531 E | * | 6/1997 | Callaghan et al. | 128/207.15 |
| 5,653,229 A | * | 8/1997 | Greenberg | 128/207.15 |

(List continued on next page.)

FOREIGN PATENT DOCUMENTS

| | | | | |
|---|---|---|---|---|
| EP | 0 284 335 A2 | | 9/1988 | |
| EP | 0 284 335 B1 | | 8/1992 | |
| NL | 6615648 | | 5/1968 | |
| WO | WO 92/13587 | | 8/1992 | |
| WO | WO 95/06492 | | 3/1995 | |
| WO | WO95/32754 | * | 7/1995 | 128/207.15 |
| WO | WO96/27404 | * | 9/1996 | 128/207.15 |
| WO | WO98/24498 | * | 6/1998 | 128/207.15 |

*Primary Examiner*—John G. Weiss
*Assistant Examiner*—Joseph F. Weiss
(74) *Attorney, Agent, or Firm*—Young & Thompson

(57) ABSTRACT

A speaker cone assembly comprises a felted paper-type cone fabricated of a composite material and a molded surround. The composite cone material contains natural fibers and synthetic fibers, where the synthetic fibers are able to chemically bond to material of the surround, thereby forming an improved bond during the molding procedure by which the surround is formed and attached to the cone. The method of preparing the composite cone material includes formulating and refining the natural fibers, preferably before adding the synthetic fibers.

14 Claims, 2 Drawing Sheets

U.S. PATENT DOCUMENTS

| | | | | |
|---|---|---|---|---|
| 5,682,880 A | * | 11/1997 | Brain | 128/207.15 |
| 5,720,275 A | * | 2/1998 | Patil et al. | 128/200.26 |
| 5,743,258 A | * | 4/1998 | Sato et al. | 128/207.15 |
| 5,749,357 A | * | 5/1998 | Linder | 128/200.26 |
| 5,791,341 A | * | 8/1998 | Bullard | 128/207.15 |
| 5,819,733 A | * | 10/1998 | Bertram | 128/207.15 |
| 5,853,004 A | * | 12/1998 | Goodman | 128/207.15 |
| 5,865,176 A | * | 2/1999 | O'Neil | 128/207.15 |
| 5,896,858 A | * | 4/1999 | Brain | 128/207.15 |
| 5,937,859 A | * | 8/1999 | Augustine et al. | 128/207.15 |
| 5,996,582 A | * | 12/1999 | Turnbull | 128/207.29 |
| 6,003,514 A | * | 12/1999 | Pagan | 128/207.15 |
| 6,070,581 A | * | 6/2000 | Augustine et al. | 128/207.15 |
| 6,095,144 A | * | 8/2000 | Pagan | 128/207.15 |
| 6,119,695 A | * | 9/2000 | Augustine | 128/207.15 |
| 6,216,696 B1 | * | 4/2001 | Van Den Berg | 128/207.14 |
| 6,240,922 B1 | * | 6/2001 | Pagan | 128/207.15 |

* cited by examiner

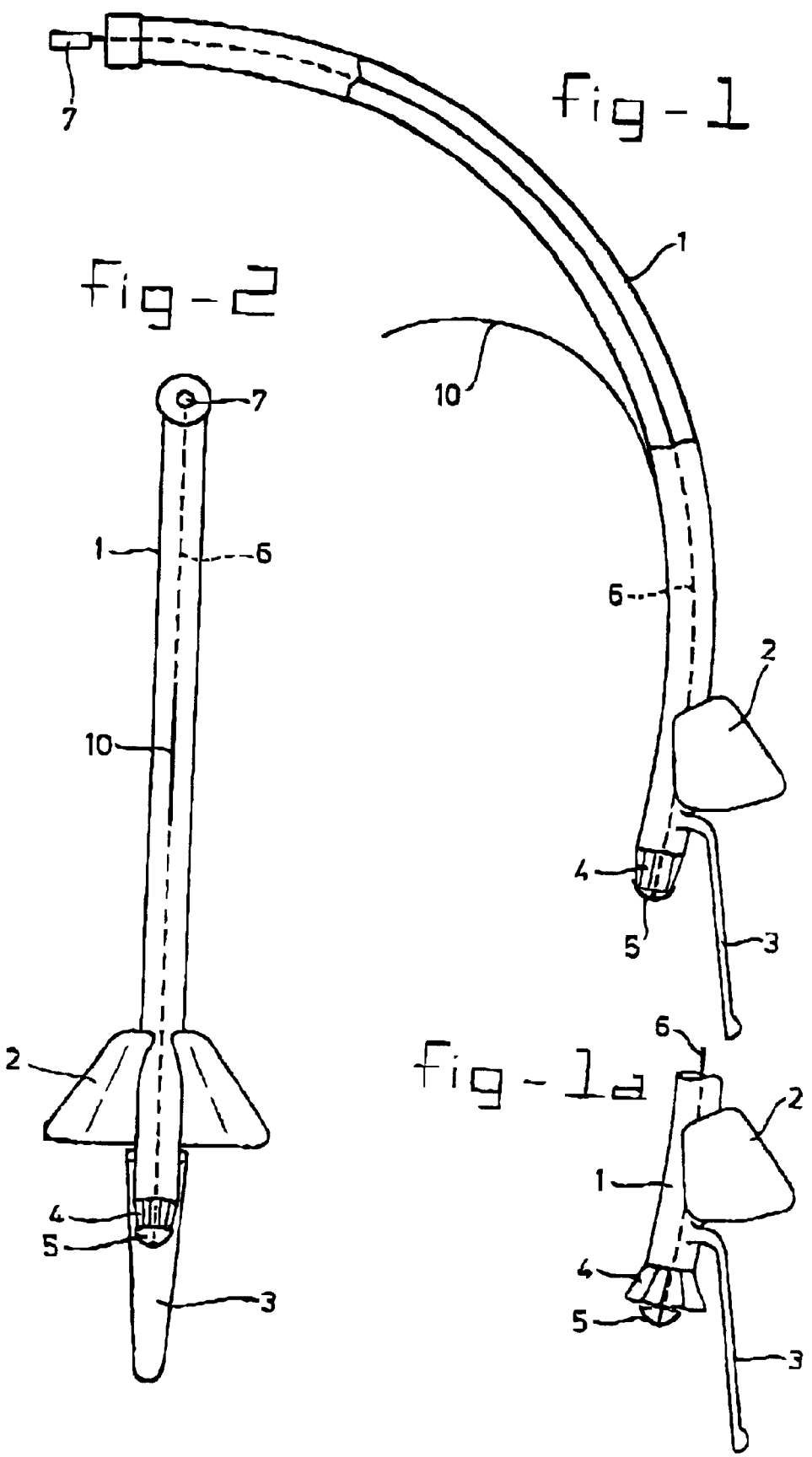

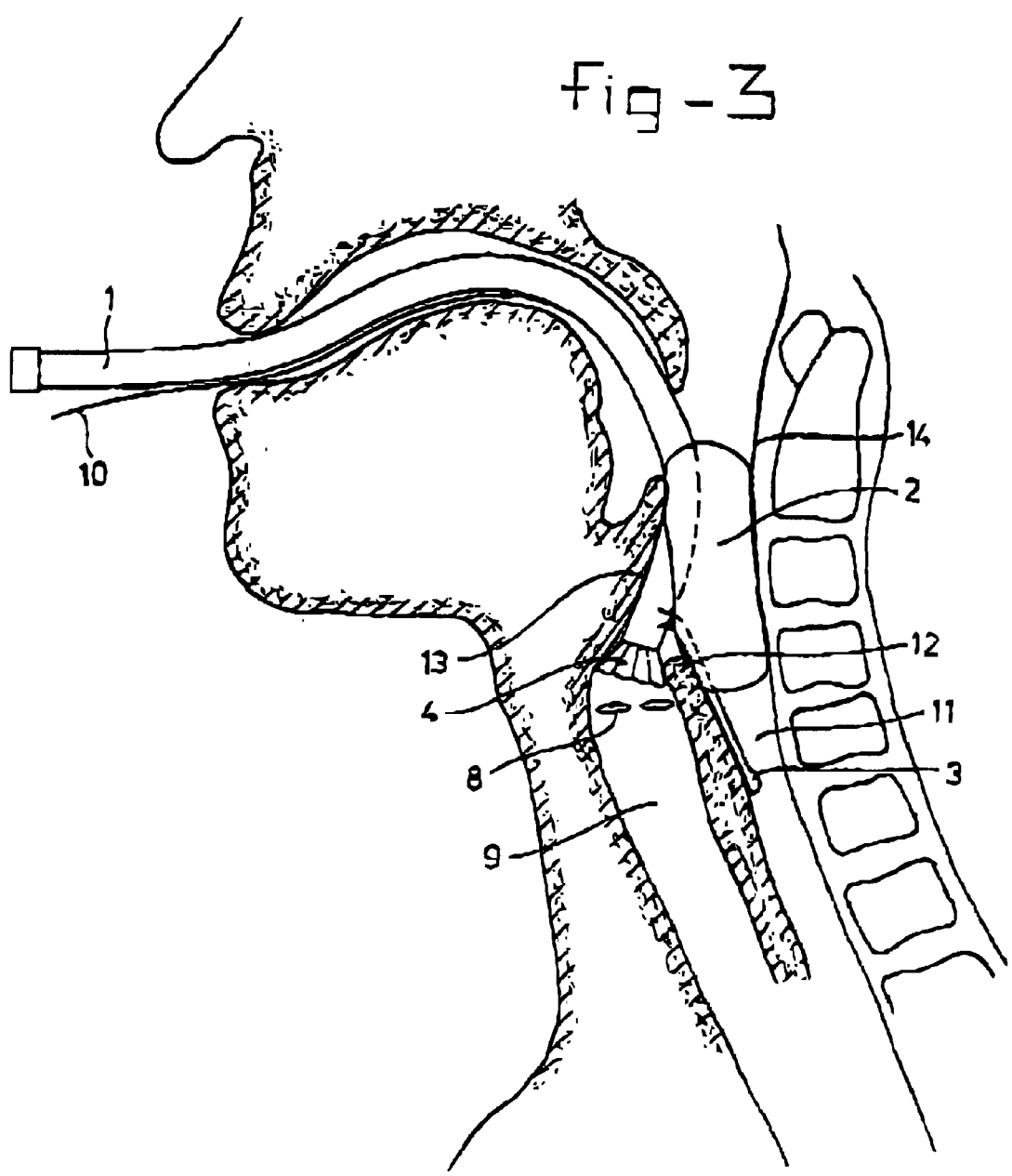
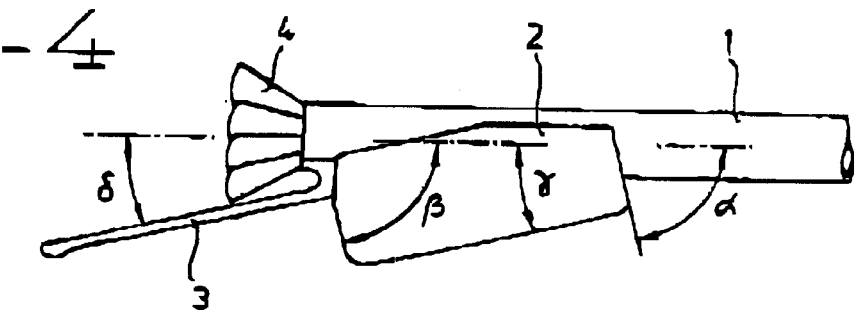

ARTIFICIAL AIRWAY DEVICE

FIELD OF THE INVENTION

The present invention relates generally to speaker cones and cone assemblies, and more particularly to a speaker cone comprising a composite material and to a cone assembly comprising the cone bonded to a surround, and to methods of making the same.

BACKGROUND OF THE INVENTION

Loudspeaker diaphragms are used to convert electric vibrations into mechanical vibration; the most common type is a cone assembly which generates acoustic sound by mechanical vibration of the cone. A cone assembly generally comprises a cone and a suspension member. The cone is a sound radiating cone which generally has a frustoconical configuration with a concave curvilinear profile. A cone is generally circular in shape, with a circular outer peripheral edge and a circular annular neck which may extend in the axial direction of the cone. This neck is at the center of the cone, and is referred to as a "voice coil inside diameter," or VCID; it is open, and may be attached to a voice coil or the like in a conventional manner. The cone is adapted to be supported on a support frame through an annular suspension member or rim, which is secured to the outer marginal edge of the cone and which has predetermined elastic or flexibility properties. Such a suspension member may also be referred to as a roll edge or as a surround. The surround may be formed as an integral generally radially directed extension of the outer marginal edge of the cone, or it may be formed as a separate annular supporting flange or rim which is then affixed to the outer marginal edge of the cone.

Various materials have been used in the construction of loudspeaker cones, including metal, woven fabric, films of plastic, and pulp comprised of natural fibers or synthetic fibers, such as carbon fibers, glass fibers, and kevlar or acrylic. Two commonly used materials are paper pulp and plastic. Paper cones are generally prepared by forming cellulose fibers of paper to a certain configuration using a mold. Such cones are also referred to as fibrous or felted paper-type cones. Plastic cones are generally prepared by one of two ways; one way is shaping pellets of plastic resin into a film, and then vacuum molding the film to form a cone, and the other way is by directly injection molding the resin form into a cone shape.

Many properties of a speaker cone depend upon the material from which the cone is constructed. Such properties include the acoustic properties, the durability of the cone, the change in the acoustic properties of the cone over time, and the ability of the cone to withstand environmental conditions such as high and low temperature, moisture and ultra violet light. The cost of manufacturing speaker cones also depends upon the cone material.

Paper cones offer several advantages over plastic cones. Typically a paper cone has a wider acoustic range, as it has more varied capabilities and greater flexibility during its manufacture in terms of controlling its stiffness. Thus, a paper cone may be made harder or softer, such as by pressing or by chemical treatments; this flexibility of manufacture does not exist with plastic, as the same treatments have no effect on plastic cones. The performance of a paper cone is also superior to that of a plastic cone, where performance is defined as how much sound level is obtained per watt of power driving the speaker; this is because paper cones are generally stiffer at lighter weights than plastic ones, and the lighter the speaker, the less power it takes to drive it. In addition, the frequency range of a paper cone is much greater for a single paper cone than for a plastic polymer cone of similar dimensions. Thus, in instances where a single paper cone in a speaker assembly might suffice, it would take two or more plastic cones to match the sound range of the single paper cone.

The advantages of plastic cones include increased versatility in appearance; such versatility exists in the greater differences in color, surface sheen, and shapes which can be obtained with plastic cones. Furthermore, the sound quality of plastic cones tends to be more uniform in different environments and over time, as the cellulose material of a paper cone is strongly influenced by humidity. However, the performance of plastic cones is typically more influenced by temperature than is the performance of paper cones.

The material of a speaker cone also influences the type of surround which can be used with it. The relatively high amplitude vibrations in the axial direction of the speaker cone, to which dynamic or moving coil-type loudspeaker cones used for mid low frequency ranges are subjected, dictates that the surround be both flexible and durable. In the past, surrounds were made from rubber; however, rubber surrounds are generally expensive. Less expensive surrounds have been made from cloth, from a thermoplastic elastomer or from polyurethane foam material. These surrounds have been pre-fabricated and then attached to the outer marginal edge of a cone with adhesives. However, such surrounds have several drawbacks. One is that the selection of starting materials is limited. Another is that fabrication of such surrounds generally involves stamping or cutting out the surround form from sheets of material, resulting in considerable waste of starting material. Yet another is that such surrounds must be attached to speaker cones, usually by means of an adhesive; however, the choice of effective adhesives is limited, and even with the better adhesives, the resulting bonds between the surrounds and the cone are often less than optimal. Furthermore, the glue adds weight to the cone. Additionally, there may be considerable variation in the alignment between the surround and the cone, which may affect acoustic properties of the cone. Finally, fabrication and attachment of such surrounds require skilled hand assembly, and thus additional time and expense of manufacture.

Alternatively, polymer based surrounds have been molded onto speaker cones. By over molding it is meant that the surround is formed and attached to a cone in a single molding process, in which the outer peripheral edge of the cone is exposed to the polymeric surround material during the molding procedure. Different types of surrounds have been used in different molding procedures with different types of cones.

In one type of molded surrounds, foam surrounds have been fabricated and attached to a felted paper-type cone by molding the surround to the cone, as disclosed in U.S. Pat. No. 5,319,718. Such surrounds are prepared by a low pressure casting process, where a liquid polyurethane foam is placed in an open mold in contact with the outer marginal edge of the cone; the mold is then closed, and the foam is expanded and cured. The result is a cone assembly with a foam surround which is molded onto the outer marginal edge of the cone, where the surround forms a mechanical bond with the cone as a result of impregnation of the surround material into the fibrous material of the cone.

In yet another type of molded surrounds, an elastomeric surround can be injection-molded onto an injection molded cone, as is disclosed in EPO 552040 B1. In this case, the surround is formed by injecting an elastomeric material into a closed mold which also contains the cone; the outer peripheral edge of the cone comes into contact with the elastomeric material. The result is a cone assembly with an elastomeric surround molded onto the outer marginal edge of the cone. As disclosed by EPO 552040 B1, the cone is also formed by injection molding, and preferably the material of the cone and of the surround are selected such that when the surround is injection molded onto the cone, the cone and the surround are chemically bonded to each other. By chemically bonded it is meant that the two become attached at a molecular level, due to cross-linking of the respective materials.

Attempts have been made to assemble paper cones with molded polymeric surrounds. However, several problems were encountered. One problem is poor attachment of an elastomeric surround with a paper cone. Attempts to injection mold an elastomeric surround onto a pure cellulose fiber material cone resulted in no bond formation, or very minimal bond formation, between the cone and the surround. By minimal bond formation it is meant that a molded elastomeric surround was easily detached or removed from the paper cone by the application of minimal force, which is quite unsatisfactory.

Another problem encountered is the formation of flash during the injection molding procedure. Flashing is defined as various points where the elastomer has seeped onto the surface of the paper cone during the injection molding procedure. Flashing is hypothesized to occur at least in part because paper is more compressible than plastic, and under the high pressure of the injection molding procedure, when the elastomer is forced into the mold cavity, the elastomer displaces the soft paper and pushes on inward, causing flashing to occur. Flashing results in an increase in cone weight, due to the presence of more material, and it is also cosmetically undesirable. Too much flash may affect performance of the cone.

Yet another problem encountered during attempts to injection mold an elastomeric surround to a paper cone is the formation of narrow witness marks during the injection molding procedure. Witness marks are the result of compressing the paper during the molding procedure; the paper is compressed when the molding tool closes upon it. Narrow witness marks are undesirable both structurally and cosmetically. Structurally, narrow witness marks are unacceptable because they result in a hinging effect, which means that the paper is depressed to the point that the cone is weakened. This weakened area affects the performance of the cone, either acoustically in affecting the sound, or in the ability of the cone to handle the power of the speaker. This weakened area is also prone to breakage. In addition, narrow witness marks are considered objectionable on a cosmetic basis, resulting in a less desirable appearance.

Thus, there is a need to provide a felted paper-type cone to which it is possible to attach a surround by molding, which results in with a strong bond between the cone and the surround. There is also a need to provide a process by which a surround may be over molded to a cone without the appearance of flashing or witness marks.

SUMMARY OF THE INVENTION

It is an object of the present invention to provide a material for manufacturing a felted paper-type loudspeaker cone to which it is possible to attach a surround by molding the surround onto the cone, where the surround bonds strongly to the cone without the appearance of flashing or the appearance of witness marks.

It is also an object of the present invention to provide a material for manufacturing a felted paper-type cone which is less susceptible to environmental conditions.

It is yet a further object of the present invention to provide a speaker cone assembly comprising a cone manufactured from the material of the invention and a surround molded onto the peripheral outer edge of the cone and strongly bonded to the material present in the cone during the molding procedure. The loudspeaker cone assembly may further include additional elements attached to the outer rim of the surround, where such additional elements are also attached to the surround during the molding procedure. Such additional elements include means for securing the surround to the speaker chassis.

These and other objects of the present invention are achieved by providing a speaker cone assembly comprising a felted paper-type cone and a molded surround which is formed and bonded to the cone during molding, where the cone material is a composite material comprising a mixture of natural fibers and synthetic fibers, and where at least some of the synthetic fibers are able to chemically bond with at least some components in the surround material.

In addition, a method for producing a composite material for use in manufacturing a felted paper-type cone is also provided, where the method comprises mixing natural fibers and synthetic fibers to form a pulp, such that at least some of the synthetic fibers are able to chemically bond with at least some components in the material of a molded surround.

Furthermore, a method for producing a speaker cone assembly comprising a felted paper-type cone and a molded surround is also provided, where the method includes molding a surround to a cone such that the surround is formed and bonded to the cone during the molding procedure, where the cone is manufactured from a composite material comprising a mixture of natural fibers and synthetic fibers, such that at least some of the synthetic fibers are able to chemically bond with at least some components in the material of the molded surround. The method may also include attaching additional elements to the outer rim of the surround during the molding procedure.

Other objects, features and advantages of the present invention will become apparent from the following detailed description. It should be understood, however, that the detailed description and specific examples, while indicating preferred embodiments of the invention, are given by way of illustration only. Indeed, various changes and modifications within the spirit and scope of the invention will become apparent to those skilled in the art from the detailed description.

BRIEF DESCRIPTION OF THE DRAWINGS

FIG. 1 is a perspective view of a typical loudspeaker cone assembly of the present invention;

FIG. 2 is a front elevational view of a typical loudspeaker cone assembly of FIG. 1;

FIG. 3 is a transverse sectional view taken substantially along line 2—2 of FIG. 2;

FIG. 4 is an enlarged fragmentary sectional view illustrating the sealing relation of a female mold and male die with the cone body in accordance with an embodiment of the present invention.

DETAILED DESCRIPTION

A composite material for manufacturing a felted paper-type loudspeaker cone is provided, where the material comprises a mixture of natural fibers and synthetic fibers and further where the synthetic fibers are able to chemically bond with material in a surround over molded to the cone. In order to achieve the desired cone characteristics, the present invention also provides a method for special processing of the natural fibers before they are used to manufacture cones. The present invention also provides a speaker cone assembly comprising a cone manufactured from the composite material and a surround, where the surround is manufactured and attached to the cone by molding, and where the surround chemically bonds to the cone during the molding process. Preferably, the surround is an elastomeric surround; more preferably, the surround is formed by high pressure injection molding. Most preferably, the surround is manufactured without the appearance of flashing or the appearance of narrow witness marks.

A typical speaker cone assembly of the present invention is shown in FIGS. 1–3. Although the cone 1 shown has frustoconical configuration with a concave curvilinear profile, other shapes are possible, such as elliptical or angular. The circular cone 1 shown in FIGS. 1–3 has a circular outer peripheral edge 3 and a circular annular neck 5 which may extend in the axial direction of the cone. This neck 5 is at the center of the cone 1, and is referred to as a "voice coil inside diameter," or VCID; it is open, and may be attached to a voice coil or the like in a conventional manner.

The speaker cone assembly also includes a surround 11, which is the means by which the cone 1 is supported on a chassis. A surround 11 is typically an annular suspension member or rim of predetermined elastic or flexibility properties which is formed so as to define a forwardly extending annular member of generally uniform radius. It is typically secured at its inner circumferential edge 13 to the outer marginal edge 3 of the cone 1, where the area of attachment 21 with the cone 1 is generally planar. Typically, the surround 11 is attached to the inner, or lower, surface 7 of cone 1, although it may be attached to the upper surface 9 of the cone 1, or to both surfaces. The area of attachment 21 is typically a circumferential area 4 extending just inward from the outer peripheral edge 3 of a cone 1. Thus, the circumferential area 4 may comprise a flattened or planar flange or rim to which the surround 11 is attached. The surround 11 often also possesses at least one curvature, or roll 15, between its inner 13 and outer 17 circumferential edges. The outer circumferential edge 17 of the surround 11 may further comprise a planar flange or rim 19, by means of which the surround 11 is attached to a loudspeaker chassis.

Previous attempts to mold a surround to paper cones of the prior art were unsuccessful, and resulted in poor bonding of the surround to the cone. It was hypothesized that this was due to the fact that the material of the paper cone consisted predominantly of cellulose, which does not form good bonds with the synthetic material of the molded surround. It was discovered that the addition of synthetic fibers to the cellulose material used to manufacture the cones, where at least some of the synthetic fibers are able to chemically bond with at least some of the components in the material of a surround molded to the cone, resulted in stronger bonding of the surround to the cone during the molding process. The resulting composite cone material, comprising a natural/synthetic fiber pulp mixture, was observed to have additional unexpected properties. For example, the composite material is more resistant to moisture. Furthermore, a speaker cone assembly, comprising a cone manufactured from the composite material and a molded, surround offers several advantages.

The surround itself doesn't degrade, warp, or allow water to pass through it. Moreover, the surround is attached to the cone in the same step in which it is formed, thereby greatly decreasing manufacturing costs, as the expense of separately forming the surround, and then hand assembling and gluing it to the cone, is no longer required. Additional cost savings are realized in the much smaller amount of starting material required to manufacture a molded surround, as the molding process results in the generation of much less waste material. Moreover, the selection of materials to use in molding any particular surround is much greater than is the selection of materials already formed into sheets which can be subsequently formed into surrounds. Finally, the process of molding the surround onto a cone also allows at the same time molding the surround to additional elements in the outer rim of the surround, such as means for attaching the surround to the chassis. These additional elements results in increased ease and security of mounting a loudspeaker cone assembly to a chassis.

Because hand assembly is not required, the resulting surround is much more uniform both in its appearance, and in its attachment to the cone. For example, there are no extraneous glue marks, and variation in placement of the surround with respect to the cone is vastly decreased. The molding process, with the improvements described below in more detail, also results in decreased flashing and witness marks. For these several reasons, the increased uniformity in appearance and the decrease in flashing and witness marks, the resulting cone assembly is much more cosmetically pleasing.

Pulp Mixture

The composite material of the present invention includes natural fibers. By natural, it is meant that the fibers originate from a naturally occurring source, such as from plants or animals. Natural fibers are well-known in the art, and include the paper pulp fibers from which paper cones are typically manufactured. Thus, examples of natural fibers include but are not limited to one or a mixture of any of the following: hardwoods, softwoods, wood kraft paper, and other natural fibrous sources such as cotton, linen, kapok, hemp, sisal, jute, kenaf, ramie, and wool fibers. Formulations of paper pulp mixtures are well known in the industry; a typical formulation of a suitable natural fiber mixture for use in preparing a composite material of the invention comprises unbleached wood kraft paper, bleached hardwood, and bleached soft wood in a final proportion of 45%, 30% and 25% dry weight, respectively.

The composite material of the present invention comprises a mixture of synthetic fibers in addition to the natural fibers, where at least some of the synthetic fibers are able to form a chemical bond with at least some of the components in the material of a surround molded onto a cone manufactured from the composite material. Thus, at least some of the synthetic fibers added to the natural fiber pulp mixture will chemically match at least some of the components in the material of the surround. By "chemically match" it is meant that at least some of the synthetic fibers will be able to form a chemical bond with at least some of the components in the material of the molded surround. The synthetic fibers in the composite cone material and the material of the surround may consist of different polymer families, as long as there is a chemical match between the cone material and the surround material. Preferably, at least some of the synthetic fibers of a particular cone composite material are of the same chemical nature as at least some of the components of the material from which the molded surround is manufactured.

By chemical nature, it is meant that at least some of the synthetic fibers are made up of the same polymeric units which are also present in the material of the molded surround. As an example, when a molded elastomeric surround for a cone is manufactured from Santoprene®, which is a particular brand of an elastomer comprising 50% polypropylene polymer and 50% EPDM rubber, at least some of the synthetic fiber added to the natural fiber pulp mixture to form the composite material for the same cone could be polypropylene or polyethylene.

The synthetic fibers added to the natural pulp mixture will also comprise at least one type of synthetic fiber. Thus, the synthetic fibers added to the natural pulp mixture may comprise from one to several different types of synthetic polymers.

Typically, materials for molded cone surrounds may comprise thermoset or thermoplastic materials. Thermoset materials can be defined as a plastic material which when heated, undergoes a chemical change and cures. It cannot be reformed, and reheating only degrades it. Thermoplastic materials can be defined as a plastic material which when heated undergoes a physical change. It can be reheated, and reformed, over and over again. Both types of materials are typically elastic in nature, and preferably an elastomer. Elastomers include a wide spectrum of rubber-like polymers that exhibit varying degrees of elasticity. A molded elastomer has the capabilities of being stretched 100%, and of retracting to within 10% of its original length within 5 minutes after being stretched 100% and held for 5 minutes. Elastomers are well known in the art, and include for example natural rubber (NR), isoprene rubber (IR), styrene-butadiene rubber (SB), neoprene (CR), nitrile rubber (NBR), butyl rubber (IIR), ethylene rubber (EPM), ethylene terpolymer rubber (EPDM), HYPALON® (CSM), acrylic rubber (ABR), polysulfide rubber (T), silicones (SI, FSI, PSI, VSI, PVSI), urethanes (U), fluoroelastomers (FPM), butadiene rubbers (BR), carboxylic (COX), and epichlorohydrin rubbers (CO, ECO). Elastomers may consist of mixtures of these and other components, as for example SEBS, which is a sytrene-ethylene butylene-styrene polymer sold by Evode Plastics Limited under the trademark Evoprene G®, and a 50% polypropylene polymer and 50% EPDM rubber mixture such as that sold by Advanced Elastomer Corporation under the trademark Santoprene®.

Thus, typical synthetic fibers present in the composite cone material would include at least some fibers which either chemically matched or were of the same chemical nature as at least some of the components of the surround material. For example, if the surround material included EPDM rubber, then the synthetic fibers could include fibers of polyethylene or polypropylene. If the surround material included SB rubber, then the synthetic fibers could include fibers of polypropylene or polystyrene. Synthetic fibers are commercially available from various sources, as for example from Mini Fibers, Inc.

The synthetic fibers are present in the composite cone material in the range of about 5% to 60% of the total final dry weight of the material. Preferably, the synthetic fibers are present at about 15–35%, and most preferably at about 30–35% of the total final dry weight of the material.

Pulp Processing

Addition of synthetic fibers to a natural fiber mixture and subsequent processing of the resulting natural/synthetic fiber pulp mixture by methods well known in the art results in the formation of cones which are too soft. By "soft" it is meant that the cones aren't stiff enough for their intended purpose. Stiffness is also referred to as rigidity, and may be thought of as the degree of flexibility of the cone material, or the strength of the cone per unit of weight, which affects the acoustic performance of the cone. Stiffness is defined as the ratio of a steady force acting on a deformable elastic medium to the resulting displacement. It is quantitated by a modulus of elasticity, or tensile modulus, which is the constant in Hooke's law, which states that stress is proportional to strain. Typically, in the speaker industry, stiffness is measured by Young's modulus, which is the ratio of simple tension stress applied to a material to the resulting strain parallel to the tension. The Young's modulus for cones manufactured from the natural/synthetic fiber pulp mixture, or composite material of the present invention, is lower than that for cones manufactured from a typical 100% natural fiber (typically paper fiber) pulp.

This observation is in contrast to the disclosure of U.S. Pat. No. 4,518,642, where it is asserted that a loudspeaker diaphragm element formed of a slurry of cellulose fibers and polypropylene fibers, where the diaphragm element is subjected to sufficient heat after drying to fuse the polypropylene fibers into a matrix, results in a stiffened diaphragm element. Although the patent asserts that "[t]his skeleton or matrix of fused thermoplastic material gives stiffness and rigidity to the resulting diaphragm," neither the term "stiffness" nor "rigidity" is defined, nor is any evidence offered to support this observation. In fact, because cones manufactured from the natural/synthetic fiber pulp mixture were observed to be too soft, the pulp mixture had to be made stronger to offset the softening effect of the added synthetic fiber. One way in which this may be accomplished is by special processing of the natural/synthetic fiber pulp mixture. Special processing includes customizing the formulation, and refining the natural fiber pulp either before or after adding synthetic fibers, although preferably before adding synthetic fibers, and subjecting the composite material to special chemical treatments either before or after cone formation, although preferably after cone formation.

Thus, in order to increase the resulting stiffness of a felted paper-type cone produced from the natural/synthetic fiber pulp mixture, the natural fiber pulp is customized and refined. Customizing means mixing a specific formulation or blend of natural fibers to achieve optimal cone performance. The formulation or blend refers to the proportion or amounts of natural fibers from different sources present in a particular pulp mixture. Refining is the processing by which natural fibers are shortened and frayed by passing the pulp mixture through discs; the shortened, frayed natural fibers result in a final felted paper-type cone of increased strength. The typical practice in the speaker cone industry is to receive paper fiber pulp pre-blended and pre-refined; these paper fibers are simply separated by beating them apart, and then used to manufacture cones. However, customizing the natural fiber blend, and refining it before or after adding the synthetic fibers, results in improved composite material for cone manufacture.

Natural pulp fibers may be obtained as loose, wet fibers. Alternatively, they may be obtained as bales of pulp sheets which were pressed and dried. Other forms of natural pulp fibers include wet-lap, sheets with varying moisture contents, and powder form. By lap, it is meant that the fibers are pressed together to form a sheet, either with the presence of moisture to varying degrees or without moisture.

The natural pulp fibers are mixed together in specific formulations, which are determined by laboratory testing to achieve specific cone characteristics determined by customer preference.

According to the special processing method of the present invention, the natural fibers of the formulated natural fiber pulp mixture are first separated; this may be accomplished by adding the formulated mixture of natural fibers and water to a large "blenderizing" vat which knocks the fibers apart. The pulp mixture is then refined, resulting in modification of the fibers in length and texture. Refining may done before or after adding synthetic fibers, although it is typically done before. Refining may be accomplished by passing the pulp mixture through discs which contain a series of grooves on their facing surfaces and which are closely spaced, for example about 1/1000 of an inch apart. The fibers may be separated and refined in a continuous loop. The fibers become frayed during refining, which results in the formation of tendrils; the presence of tendrils on the fibers in turn results in more interconnections between the fibers, and a stronger felted paper-type cone material with improved acoustic and/or mechanical properties of the cone. The degree of refining is precisely controlled, and each batch of the resulting refined pulp is tested in the laboratory to control its quality. One measure of the degree of refining achieved is "freeness" as determined by the Williams Freeness test. In this test, a measured volume of a solution of the refined natural fibers is placed over a filter, and the time for the liquid to drain through the filter determined. The more frayed the fibers are, the longer it will take the liquid to drain. The strength of the felted paper-type material produced from the refined pulp may be determined by the Mullen test. In this test, the paper is clamped down, and the force required to break the paper determined by use of an elastomeric measuring device. This test is used to measure the strength of both natural fiber paper and paper manufactured from the composite material of the invention.

The synthetic fibers are generally added after the natural fibers are refined. The synthetic fibers may be added as loose fibers, or they may be added as wet lap or dry lap. The fibers are separated by pulpers, which effectively blenderize them and mix them with the natural fibers. It is believed that the fibrous form of the synthetic fibers intertwines and entangles with the natural fibers.

Additional materials may also be added to the pulp, either before or after the synthetic fibers are added. Such components are well-known in the art, and include coloring components and fillers. Coloring components include dyes, such as aniline dye, and dye binding constituents, such as aluminum sulfate. Fillers may be added to impart additional strength, and thereby to affect acoustic properties, or to affect surface appearance, such as to add sheen. Fillers include mica and crushed clam shells.

Formation of a Cone

The making of felted or fibrous cones is an old, well established technology as is disclosed by U.S. Pat. No. 1,872,533, which is hereby incorporated by reference in its entirety. A felted paper-type speaker cone may be formed from the composite material of the invention by a conventional felting process, as is typically utilized in the manufacture of paper cones. In such a process, a cone may be formed with a machined form, such as a screen, having the desired configuration of the finished cone. The form is submerged in an aqueous suspension of the composite natural/synthetic fiber pulp mixture of the present invention and suction is applied to one side of the form to draw the suspension onto the form. Felting of the fibers occurs on the form on the side opposite the side through which the suction is applied, until the desired thickness of the fibers is built up on the form to establish a peripheral wall of generally uniform thickness from the free edge of the neck portion to the outer marginal edge of the cone. The felted form is then dried sufficiently to enable removal of the fibrous cone from the form. Conventionally, the cone is formed to a predetermined thickness for a particular size or shape. The final product of this process is a formed and dried cone.

A cone prepared from the composite material of the present invention generally exhibits decreased stiffness when compared to a cone prepared from conventional paper pulp material, and therefore may be chemically treated to increase its stiffness and rigidity. Although the degree of stiffness affects the acoustic properties of a cone, the final acoustic performance depends upon a number of factors, which include the cone material, its surface treatment, and its geometry. The special processing of the composite material of the invention, which includes formulating and refining the natural fiber pulp, increases the stiffness of a cone manufactured from the material. Additional stiffness may be imparted by chemical treatments which are well known in the art; such treatments are selected to achieve the desired degree of stiffness of the final cone. For example, stiffening a cone may be accomplished by chemically treating the cone with lacquers. The degree of stiffness is controlled by the type of lacquers selected, how much is used, and which parts of a cone are treated. Additional chemical treatments which are well known in the art, and which result in further improvements to and enhancements of the cone, include chemically treating a cone with acrylics and various waterproofing agents and dampening agents. Chemical treatments include submersing the cone into a chemical treatment, or dipping it into a bath to adsorb various chemicals. Different areas of a cone may be treated differently, to result in specific final cone properties.

Optional further processing of the cone may be done before or after the chemical treatments described above, although such processing is more commonly done afterward. One such further processing is pressing. With reference now to FIGS. 1 and 2, a felted paper-type cone initially formed as described above, where a vacuum is applied to the inner or lower surface 7, is typically smooth on this surface, and rough on the outer, or upper, surface 9. Pressing a formed, dried cone 1 smooths the outer surface 9, thereby presenting a cosmetically more pleasing cone. Pressing is accomplished by placing a molded cone between matched dies which allow clearance for the cone to its final thickness. The cone is then subjected to heat for a period of time to effect the pressing; typically, the cone is subjected to 200° to 400° C. for 2 to 8 seconds. Pressing increases the density of the cone, which affects the sound properties of the cone. Pressing also improves the sheen and thus the appearance of the cone.

Formation of a Surround

With reference to FIGS. 1–3, a surround 11 in a speaker cone assembly is typically an annular suspension ring formed so as to define a forwardly extending annular surface which is generally of uniform radius. It is typically attached at its inner circumferential edge 13 to the outer marginal edge 3 of the cone 11, typically at the inner, or lower, surface 7; alternatively, the surround 11 may be attached to the outer, or upper, surface 9 of cone 1, or to both surfaces. The outer circumferential edge 13 of the surround 11 may further comprise a planar flange or rim 19, by means of which the surround 11 is attached to a loudspeaker chassis.

The outer rim 19 may also comprise additional elements, such as a paper gasket, a rubber gasket, a plastic gasket, a foam gasket, lugs, or the like, which may be added after the surround is attached to the cone, or which may be attached at the same time that the surround is attached to the cone. Such additional elements may be useful, for example, for attaching the speaker cone assembly to a chassis. Attachment of such additional elements such as gaskets has been an additional costly step in the manufacture of loudspeaker cone assemblies; thus, gaskets have been difficult to attach with adhesives, and required further hand assembly. By attaching a gasket during the over molding step in which a surround is both formed and attached to a cone, the cost of processing is significantly decreased. Surprisingly, the bond of such a gasket to the surround is often also superior to one attached by hand, as it is stronger. The strength of the bond between a gasket and a surround depends upon the material of each, and is thought to be due to a mechanical bond or to a chemical bond, or to both.

The surround is formed by molding such that it becomes bonded during the molding process to a cone comprising the composite material of the present invention. Typically, the surround may be formed from plastic foam, as for example by low pressure casting molding, or it may be formed from elastomeric material by injection molding, using materials and methods well known in the art. The material for the surround is selected in conjunction with the composite material of the present invention from which the cone is manufactured, such that during formation and attachment of the surround to the cone, the surround becomes bonded to the cone. Preferably, the surround is chemically bonded to the cone. Chemical bonding means that at least some components of the material of the surround form chemical bonds with at least some of the synthetic fibers of the composite material of the cone. Typical materials for a foam surround include polyurethane. Typical materials for an elastomeric surround have been described previously. Preferably, such materials include a sytrene-ethylene butylene-styrene polymer (SEBS) such as that sold by Evode Plastics Limited under the trademark Evoprene G®, and a 50% polypropylene polymer and 50% EPDM rubber mixture such as that sold by Advanced Elastomer Corporation under the trademark Santoprene®. Preferably the elastomer has a shore A hardness of between about 40 and 60.

The material of the surround may contain components in addition to the components described above. These components may include reinforcements, which are typically added to enhance physical strength properties, and fillers, which are typically added to enhance properties other than strength. Fillers may include colorants, plasticizers, heat stabilizers, antioxidants, flame retardants, ultraviolet light absorbers, antistatic agents, blowing agents, and lubricants. Both reinforcements and fillers are well known in the art, and the selection of what type to add depends upon the desired characteristics of the surround. Reinforcements and fillers may already be present in surround material selected for use with a particular cone composite material, or they may be added just prior to the molding process.

A surround may be formed from a plastic foam material by a low pressure casting process by techniques which are well known in the art, such as is described by U.S. Pat. No. 5,319,718 which is hereby incorporated in its entirety. The plastic foam material may comprise a closed cell material such as a polyurethane; one example is Polyurethane System product identification No. SSF-1782, which is a liquid state foam obtainable from Plast-O-Meric, Inc., North Baltimore, Ohio. In one embodiment, with reference to FIGS. 1–3, a cone 1 of the composite material of the invention is placed into one half of a mold which has an annular channel or cavity configured in the shape of the surround 11, such that the outer marginal edge 3 of the cone 1, at the circumferential area 4, is exposed to the annular cavity. A predetermined quantity of liquid plastic foam is deposited into the cavity, and the mold is closed and sealed with the other half of the mold. The foam is then cured under pressure and temperature conditions such that the resulting surround 11 is over molded onto the cone 1, and the surround 11 is mechanically and chemically bonded the cone 1. The configuration of the mold defines the shape of the surround 11 and defines the degree of the attachment of the surround 11 to the cone 1 at the outer circumferential area 4. Thus, the configuration of the mold determines the surface of the outer circumferential area 4 at the outer marginal edge 3 of the cone 1 which is exposed to the surround material, and how much of the area 4 is exposed to the surround material. The surround 11 may be over molded onto either the inner or lower surface 7 of the cone 1, or to the outer or upper surface 9 of the cone 1, or to both surfaces to the same or different extents. In the latter embodiment, the inner circumferential edge 3 of the surround 11 forms a "sandwich" around the outer marginal edge 3 of the cone 1. Preferably, the surround 11 is over molded to the inner or lower surface 7 of the outer marginal edge 3 of the cone 1.

Preferably, the surround is formed from elastomeric material and utilizes injection molding techniques which are well known in the art, such as is described in EPO 552040B1, which is hereby incorporated in its entirety. Generally and with reference to FIGS. 1–3, such a surround 11 is made by placing a cone 1 in a mold such that the outer peripheral edge 3 of the cone 1 at the circumferential area 4 is exposed to a cavity which defines the surround 11, closing the mold, and injecting a molten elastomeric material into the cavity so that the material fills the mold and comes into contact with the circumferential area 4 of the cone 1. In a similar manner as was described for low pressure molding, the configuration of the injection mold defines the shape of the surround 11 and defines the degree of the attachment of the surround 11 to the cone 1 at the outer circumferential area 4. Thus, the configuration of the mold determines the surface of the outer circumferential area 4 at the outer marginal edge 3 of the cone 1 which is exposed to the surround material, and how much of the area 4 is exposed to the surround material. The surround 11 may be over molded onto either the inner or lower surface 7 of the cone 1, or to the outer or upper surface 9 of the cone 1, or to both surfaces to the same or different extents. In the latter embodiment, the inner circumferential edge 3 of the surround 11 forms a "sandwich" around the outer marginal edge 3 of the cone 1. Preferably, the surround 11 is over molded to the inner or lower surface 7 of the outer marginal edge 3 of the cone 1.

A surround may also be formed form a foamed elastomeric material. Such material is foamed during the injection procedure by pumping a gas, such as nitrogen, or a liquid, such as water, into the stream of material by techniques well-known in the art. An example of material which may be foamed is G7705, which is a block co-polymer comprising styrene:ethylene:butylene:styrene (SEBS) and which is available from GLS Corporation. A foamed elastomer results in a decrease in manufacturing cost, since less material is required to produce a foamed surround which is less dense than a non-foamed surround.

The molding process may be enhanced by pressing a formed and dried cone, as described above. Pressing not improves the appearance of a cone but also allows the cone to fit smoothly and snugly into a mold for molding a surround, thereby allowing a tighter fit between the two surfaces of the cone and the mold. The tighter fit is important as it prevents reversion of elastomer during injection molding of an elastomeric surround. By "reversion" it is meant that some elastomer is deposited on the wrong side of a cone, or on the side opposite to the side which is over molded with a surround.

Pressing a cone also decreases flashing. Flashing is defined as various points where the elastomer has seeped onto the surface of a felted paper-type cone during injection molding. Flashing is due in part to slight or small irregularities, or cavities, in the surface of the cone which are filled with elastomer during the injection molding process. Because pressing the formed cone results in a cone body of consistent thickness, with many fewer irregularities of greatly decreased variability and of much smaller size, there is less flashing.

The configuration of the mold may also control to some extent the degree of flashing and the appearance of witness marks which are formed on the cone during injection molding. Flashing is also believed to occur at least in part because the material of a felted paper-type cone is compressible, and under the high pressure of injection molding, when the elastomer is forced into the mold cavity, the elastomer displaces the felted paper-type material and pushes on inward and upward on the cone body in the direction of the neck, causing flashing to occur. In this case, flashing may be controlled by the shut off mechanism of the die, as shown in FIG. 4. When a cone 1 is placed into the injection molding apparatus, the surface of the mold 31 in contact with the lower or inside surface 7 of the cone 1 is tightly appressed to the entire cone surface, except at the circumferential area 4 at the marginal edge 3 of the cone 1; it is this circumferential area 4 which is exposed to the elastomer, and which is thus over molded by the elastomer. The configuration of the surface of the mold 31 results in less compression of circumferential area 4 than of the remainder of the cone body 2, resulting in a slightly increased thickness of the circumferential area 4 as compared to the remainder of the cone body 2. The slightly thicker edge of the circumferential area 4 can act as a seal, or positive shut-off, to prevent elastomer from leaking further up onto the cone body 2. The result is an elimination or decrease of flashing.

Witness marks are due to the zone of compression of the shut off mechanism of the mold. This zone of compression is narrow in the prior art, which discloses the use of annular pinch beads, annular grooves with resilient seals, or annular spring biased compression rings and the like, as die shut off mechanisms. These mechanisms result in a narrow zone of compression near the outer peripheral edge of a cone during injection molding of a surround to a cone, resulting in the appearance of narrow witness marks. In the mold configuration shown in FIG. 4, the surface of the mold 31 in contact with the lower or inside surface 7 of the cone 1 is tightly appressed to the entire remainder of the cone surface 7, from the outer edge of the circumferential area 4 to the neck 5 of the cone 1. This area of tight appression, or zone of compression 33 of the cone body 2, is large in comparison to the narrower zones of compression of the prior art. Thus, the occurrence of narrow witness marks are decreased or eliminated by extending the zone of compression 33 to the neck 5 of the cone 1 as occurs with the shut-off mechanism of the die of the present invention.

Improved Bond Formation

The strength of the bond between a cone and its surround may be determined in a number of ways. One method of measuring bond strength utilizes a tensile tester, in which the force required to observe tearing or failure of either the bond or the substrate can be quantified. Bond failure means that the surround separates or tears from the cone, leaving the material of both the cone and the surround substantially intact. Substrate failure means that the material of either the cone or the surround tears, or fails, before the bond fails. With the tensile tester, the cone and the surround are placed into two separate clamps, with the surround in a lower clamp, and a measurable force is applied to the cone in an upward direction. The amount of force at which the bond fails, or at which the substrate fails, can then be quantified. A stronger bond is indicated by increased force which can be applied before the bond fails, or by the occurrence of substrate failure before bond failure.

Previously, attempts to attach surrounds to typical paper cones resulted in a bond between the surround and the cone which was unacceptable. Either the surround itself failed, or tore, as when a plastic foam surround was glued to a cone, or the bond itself failed, so that the surround separated from the cone, leaving both the surround and the cone essentially intact, as happened when an elastomeric surround was injection molded onto a typical paper cone.

The presence of synthetic fibers in the composite cone material of the present invention results in formation of an improved bond of surround molded to a cone. By "improved bond" it is meant that under pressure, either the surround or the cone material will fail before the bond will fail; in other words, substrate failure occurs before bond failure. The formulation of the natural/synthetic fiber pulp mixture used in the composite cone material of the present invention may be optimized by selecting for increased or improved bond strength, as for example by utilizing the tensile tester as described above.

It is believed that the improved bond between the cone and the surround is due in part to formation of secondary chemical bonds between the cone and the surround, in which at least some of the synthetic fibers in the composite cone material of the present invention bond with at least some of the synthetic polymer present in the surround material. This type of bond is also referred to as a molecular bond. A secondary chemical bond is formed during the molding procedure between the mixture of melted polymers of the surround material and the solidified synthetic fibers present in the composite cone material.

It is further believed that the improved bond between the cone and the surround is also due in part to a stronger mechanical bond. A mechanical bond is formed by impregnating the composite cone material with the material of the surround, which results in intermingling of the fibers of the composite cone material with material of the surround. The improvement in mechanical bonding is thought to be due to several factors. One is a result of the initial special processing of the natural fibers before adding the synthetic fibers; this special processing results in natural fibers which are highly frayed and which can thus form more interconnections with the material of the surround. Another way in which the mechanical bond between a cone and its surround is improved is by leaving a portion of the outer marginal edge of the cone compressed less than the remainder of the cone body, as occurs during injection molding. The less compressed edge is thus thicker than a more compressed edge, and so exposes a larger surface area to the elastomeric surround material; this allows the elastomer greater access to the cone material, resulting in increased impregnation of the elastomer into the edge of the cone. The net result is a stronger mechanical bond. In addition, the increased impregnation of the cone edge by the elastomer also allows for increased chemical bond formation between the surround and the cone.

EXAMPLES

Typical speaker cone assemblies comprise a cone and a molded elastomeric surround. The composite cone material of the present invention typically comprises a mixture of natural fibers and synthetic fibers, where the natural fibers are paper pulp fibers obtained from natural wood fibers and preferably comprise unbleached wood kraft paper, bleached hardwood, and bleached soft wood fibers in a final proportion of 45%, 30% and 25% dry weight, respectively, and where the synthetic fibers are polypropylene, and where the natural fibers and synthetic fibers are present in about 70% and 30% of the final composite cone material dry weight, respectively. The elastomeric material typically comprises either G7705, which is a block co-polymer comprising styrene:ethylene:butylene:styrene (SEBS) and which is available from GLS Corporation, or Santoprene®, which is an EPDM rubber and polypropylene plastic and which is available from Advanced Elastomer Corporation. Formation of the composite cone material of the present invention and formation of the cone are as describe above. The surround is over molded to the cone by injection molding as described above.

The embodiments of the invention in which an exclusive property or privilege is claimed are defined as follows:

1. An artificial airway device comprising:
    a tube having a first end for insertion into a user's mouth and trachea, and a second end tobe disposed outside of the user's oral cavity, said tube having a length for introducing said first end into an entry to the user's trachea;
    an inflatable sealing ring at said first end of said tube, said inflatable sealing ring forming a seal between a wall of said tube and a wall of the user's pharynx; and
    wherein, said sealing ring has a first, uninflated state and a second, inflated state, in said first state, said sealing ring terminates before said first end of said tube, and in said second state, said sealing ring extends beyond said first end of said tube, and in said second state having a shape and dimensions to substantially fit into the entry of the user's trachea and against an underside of the user's epiglottis.

2. The artificial airway device according to claim 1, wherein an angle is formed between the sealing ring and the first end of the tube, in the second state.

3. The artificial airway device according to claim 2, wherein said sealing ring, in said second state, essentially has a shape of a trapezium, in longitudinal section along a longitudinal axis of said tube, with a first sealing ring side facing away from said first end of said tube, and a second sealing ring side facing towards said first end of said tube, said first sealing ring side being smaller than said second sealing ring side.

4. The artificial airway device according to claim 3, wherein said first sealing ring side forms an angle $\alpha$ of less than 90° with the longitudinal axis of the tube.

5. The artificial airway device according to claim 3, wherein said second sealing ring forms an angle $\beta$ of less than 90° with the longitudinal axis of the tube.

6. The artificial airway device according to claim 3, wherein a first wall of said sealing ring forms an angle $\gamma$ with respect to the longitudinal axis of the tube so that a distance between said first wall of said sealing ring and said tube increases in a direction towards the first and of the tube when said device goes from said first state to said second state.

7. The artificial airway device according to claim 1, further comprising a strip attached to said tube, at the first end of said tube, in said second state, said strip being introduced into the user's esophogus and said tube extending towards the user's trachea.

8. The artificial airway device according to claim 7, wherein said strip is L-shaped and in said first state of the artificial airway device, forms an angle $\delta$ with longitudinal axis of the tube, said angle $\delta$, when the tube has been introduced into the user's larynx and the sealing ring has been inflated, is reduced to approxiamately 0°.

9. The artificial airway device according to claim 1, further comprising a sealing member at the first end of the tube to seal the entry to the user's trachea.

10. The artificial airway device according to claim 9, wherein said sealing member comprises a ring of mutually overlapping, protruding, flexible flaps.

11. The artificial airway device according to claim 10, further comprising a cap that surrounds the flexible flaps when the sealing member is being introduced, said cap being connected to a thread that leads to the first end of the tube.

12. The artificial airway device according to claim 10, wherein the thread is hollow.

13. The artificial airway device according to claim 8, wherein the angle $\delta$ is between 10° and 20°, in said first, uninflated state.

14. The artificial airway device according to claim 1, wherein the ring only partially circumferentially extends around the tube.

* * * * *